(12) United States Patent
Sussman et al.

(10) Patent No.: US 9,878,075 B2
(45) Date of Patent: Jan. 30, 2018

(54) VACUUM CONTROL METHOD FOR SURGICAL HAND PIECE

(71) Applicant: Alcon Research, Ltd., Fort Worth, TX (US)

(72) Inventors: Glenn Robert Sussman, Laguna Niguel, CA (US); John Morgan Bourne, Irvine, CA (US); Mikhail Boukhny, Laguna Niguel, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 470 days.

(21) Appl. No.: 13/709,752

(22) Filed: Dec. 10, 2012

(65) Prior Publication Data
US 2014/0163454 A1 Jun. 12, 2014

(51) Int. Cl.
*A61B 17/20* (2006.01)
*A61M 1/00* (2006.01)
*A61F 9/007* (2006.01)

(52) U.S. Cl.
CPC ....... *A61M 1/0031* (2013.01); *A61F 9/00745* (2013.01); *A61M 1/0039* (2013.01); *A61M 1/0058* (2013.01); *A61M 2210/0612* (2013.01)

(58) Field of Classification Search
CPC .... A61M 1/00; A61M 1/0031; A61M 1/0058; A61M 1/0039; A61M 2210/0612; A61M 2210/0162; A61M 37/0092; A61F 9/009; A61F 9/00745; A61F 9/007

USPC .......................................................... 604/22
See application file for complete search history.

(56) References Cited

U.S. PATENT DOCUMENTS

| | | | | |
|---|---|---|---|---|
| 5,676,650 A | * | 10/1997 | Grieshaber | A61M 1/0058 417/205 |
| 6,241,700 B1 | * | 6/2001 | Leukanech | A61F 9/00745 604/19 |
| 6,425,883 B1 | * | 7/2002 | Urich | A61F 9/00736 604/118 |
| 2001/0014785 A1 | * | 8/2001 | Sussman | A61F 9/00736 604/22 |
| 2007/0179432 A1 | * | 8/2007 | Bar Or | A61B 1/00068 604/30 |
| 2009/0032121 A1 | * | 2/2009 | Chon | A61M 39/24 137/529 |
| 2010/0076471 A1 | * | 3/2010 | Bourne | A61F 9/00745 606/161 |
| 2010/0185150 A1 | * | 7/2010 | Zacharias | A61M 1/0031 604/119 |
| 2010/0280435 A1 | * | 11/2010 | Raney | A61M 1/0031 604/22 |
| 2010/0312170 A1 | * | 12/2010 | Maaskamp et al. | 604/22 |
| 2011/0137231 A1 | * | 6/2011 | Sorensen | A61F 9/00745 604/22 |

\* cited by examiner

*Primary Examiner* — Kevin C Sirmons
*Assistant Examiner* — Tiffany Legette-Thompson

(57) ABSTRACT

A surgical hand piece is described that maintains a vacuum pressure within the hand piece at a selected level. A check valve is provided substantially near an inlet of an integrated aspirating pump. The check valve opens to introduce fluid into the hand piece to maintain the vacuum pressure within the hand piece at or above the selected level so as to prevent or substantially reduce post-occlusion flow.

18 Claims, 3 Drawing Sheets

VACUUM CONTROL METHOD FOR SURGICAL HAND PIECE

FIELD OF THE INVENTION

This disclosure relates generally to the field of surgical hand pieces, and more particularly, to a surgical hand piece adapted to maintain vacuum pressure within the hand piece at a selected level during a surgical procedure.

BACKGROUND OF THE INVENTION

The human eye functions to provide vision by transmitting light through a clear outer portion called the cornea, and focusing the image by way of a crystalline lens onto a retina. The quality of the focused image depends on many factors, including the size and shape of the eye and the transparency of the cornea and the lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During a phacoemulsification procedure, a probe tip of a phacoemulsification hand piece is inserted into the anterior segment of the eye through a small incision in the outer tissue of the eye. A user, such as a surgeon, brings the tip of the probe into contact with the lens of the eye, so that the vibrating tip fragments the lens. The resulting fragments are aspirated out of the eye through the interior lumen of the probe, along with irrigation solution provided to the eye during the procedure.

Throughout the procedure, irrigation fluid is introduced into the eye. This irrigation fluid prevents the collapse of the eye during the removal of the emulsified lens. The irrigation fluid also protects the eye tissues from the heat generated by the vibrating of the ultrasonic cutting needle. Furthermore, the irrigation fluid suspends the fragments of the emulsified lens for aspiration from the eye.

A problem that occurs during the phacoemulsification process arises from a blockage, or occlusion, of the probe's lumen. As the irrigation fluid and emulsified tissue is aspirated away from the interior of the eye through the probe's lumen, pieces of tissue that are larger than the diameter of the lumen or harder pieces of tissue may become lodged in the probe, obstructing flow therethrough. While the probe is clogged, pressure drops (i.e., vacuum builds). When the material within the needle becomes dislodges, a rapid pressure change occurs within the anterior chamber of the eye results. This rapid pressure change can result in aspiration of a relatively large quantity of fluid and tissue out of the eye very quickly and is referred to as post-occlusion surge. This post-occlusion surge can, in some cases, cause injury to the eye, such as, causing the eye to collapse and/or causing the lens capsule to be torn.

SUMMARY OF THE INVENTION

The present disclosure generally relates to a surgical hand piece for use in surgical procedures, for example, phacoemulsification procedures. The surgical hand piece may include a hand piece body and a probe operatively coupled to the hand piece body. The probe may include a lumen. An aspiration passage may extend through the hand piece body. The lumen may be in communication with the aspiration passage. An aspiration pump may be included within the hand piece body. The aspiration pump communicates with the aspiration passage. The aspiration pump is operable to generate an aspirated flow into and through the probe and along the aspiration passage.

The hand piece may include a check valve. The check valve may be in communication with the aspiration passage to maintain pressure within the hand piece at or above a selected level. The check valve may be a one-way check valve. The check valve may open in response to a pressure condition within the aspiration passage to introduce fluid thereinto. For example, the check valve may be operable to open when the pressure within the aspiration passage drops below the selected level. The check valve may remain open until the pressure within the aspiration passage increases to or above the selected level.

The hand piece is readily responsive to a change in pressure within the hand piece and is operable to maintain pressure within the hand piece at or above a selected level so that post-occlusion surge is eliminated or substantially reduced.

Various objects, features and advantages will become apparent to those skilled in the art based on the following drawings and detailed description.

DETAILED DESCRIPTION

Figure 1:
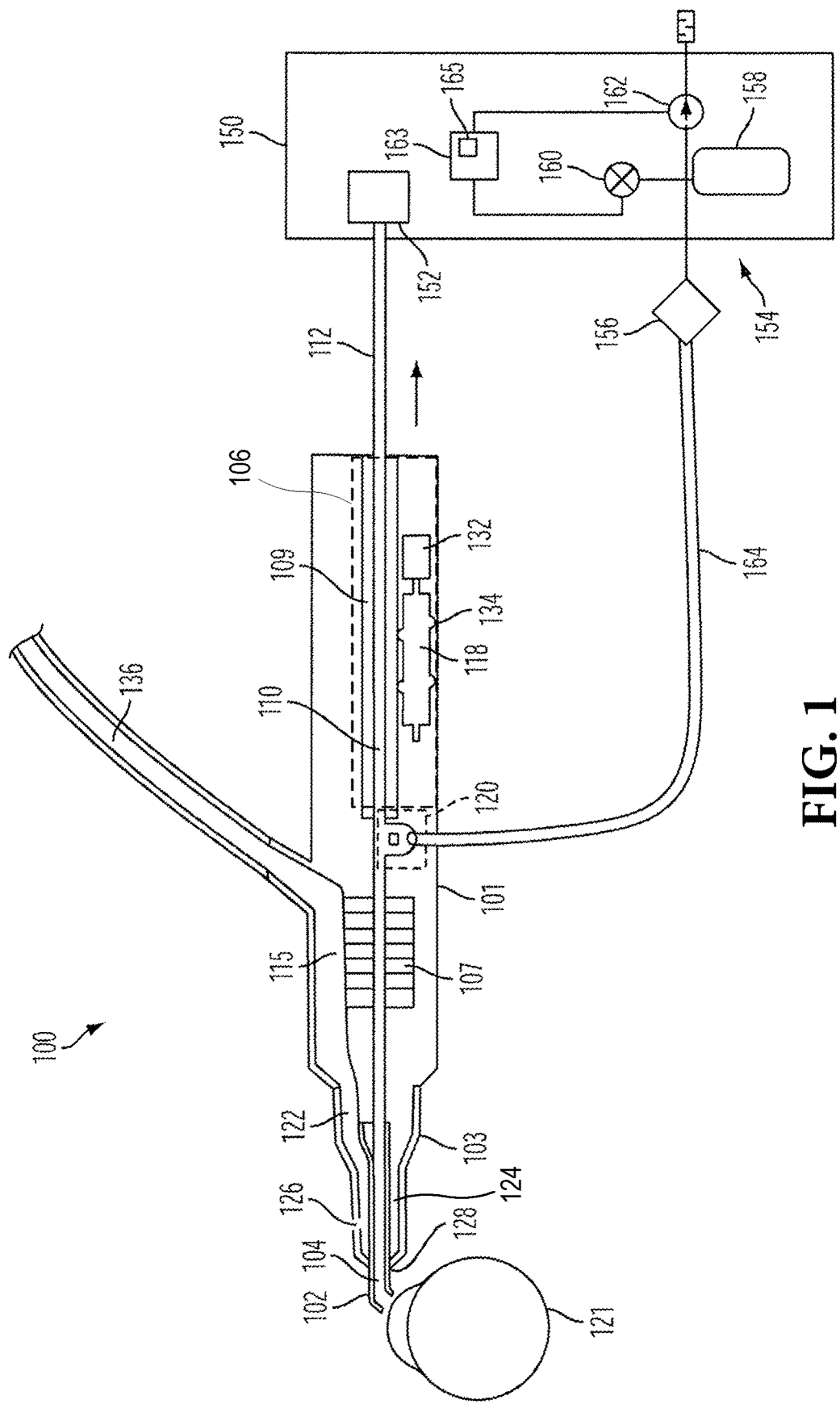
FIG. 1 shows an example phacoemulsification system that includes a surgical hand piece show in cross-section.
Figure 2:
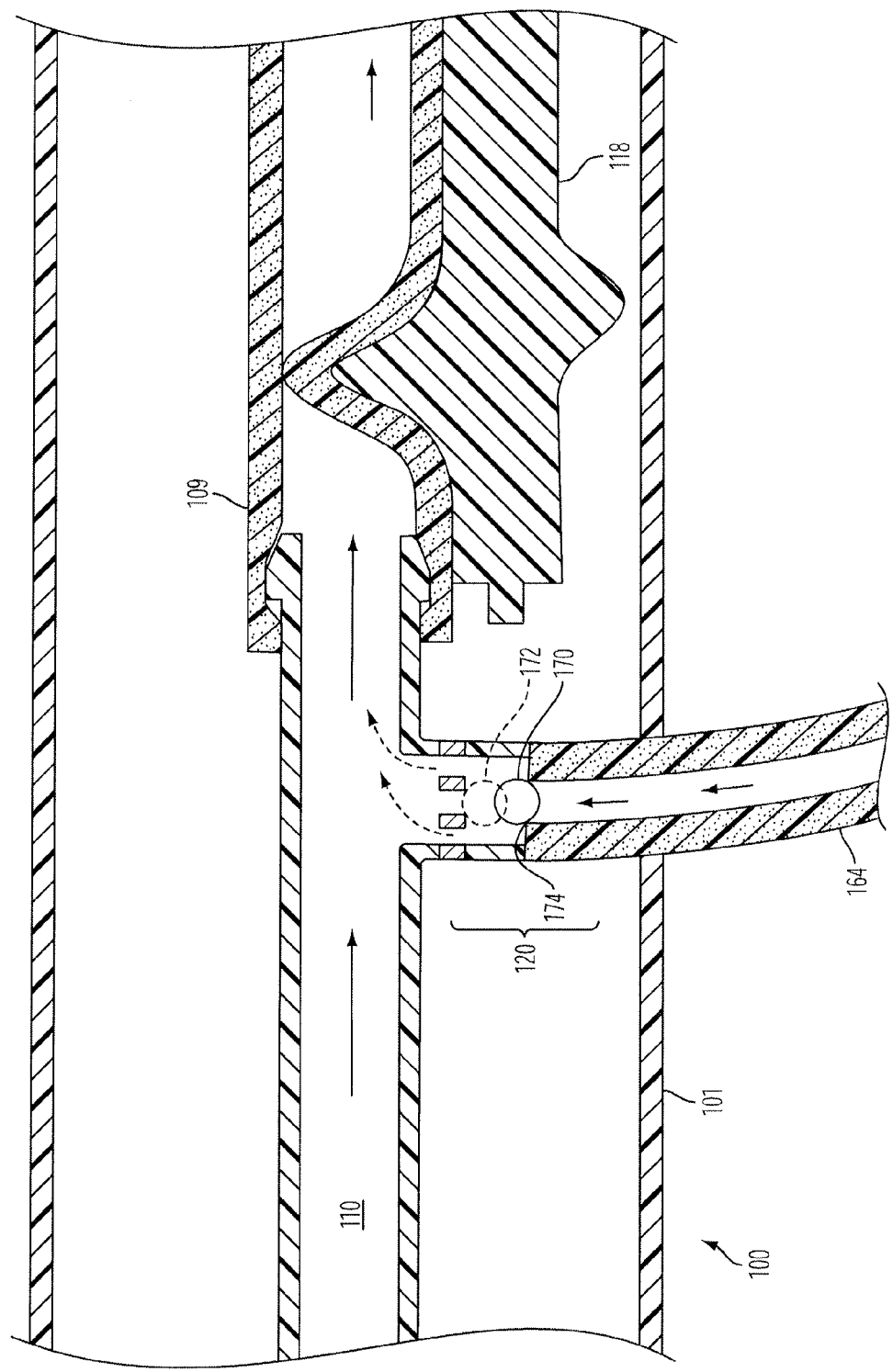
FIG. 2 is a detail view of a portion of the hand piece of FIG. 1 that includes an example check valve.

As illustrated in the FIGS. 1 and 2, an example aspirating surgical hand piece 100 is shown. The hand piece 100 is configured to maintain a pressure therein at a selected level. For example, the selected level may be a predetermined pressure level. The occurrence of a decrease increase in pressure, such as a rapid decrease in pressure caused by an obstruction, is relieved by operation of a check valve, such as check valve 120, provided on the hand piece 100 to prevent post-occlusion surge. Thus, the check valve 120 is operable to rapidly respond to changing pressure levels within the hand piece 100. Thus, the check valve 120 is operable to rapidly prevent a decrease in pressure within the hand piece 100, thereby eliminating or substantially reducing post-occlusion flow resulting when an obstruction within the hand piece is cleared. As a result, damage to the eye is avoided.

The check valve 120 included with the example hand piece 100 shown in FIGS. 1 and 2 is a ball-type valve. Accordingly, the present description is made with respect to this example implementation. However, the scope of the disclosure is not so limited. Rather, the scope of the present disclosure includes numerous other types of valves that are operable to actuate in response to changing pressure conditions, particularly pressure changes occurring within a conduit (e.g., vacuum pressure changes). Various other examples valves are discussed herein. Further, still other valves falling within the scope of the disclosure would be recognized by those skilled in the art.

FIG. 1 shows an example phacoemulsification hand piece 100 having an integrated aspiration pump 106. The hand piece 100 may include a body 101 and a probe 102 operatively coupled to the hand piece body 101 and projecting therefrom. The probe 102 may be a hollow needle or cannula that defines a lumen 104. The lumen 104 is operable to pass fluids and tissues removed from an eye, such as eye 121. The lumen 104 is in fluid communication with a passage 110. Materials removed from the eye 121 through the lumen 104 are conducted through the hand piece 100 via the passage 110. A length of flexible tubing 109 may define at least a portion of the passage 110. The materials are removed from the hand piece 100 via a conduit 112 coupled to the hand piece 100 and in fluid communication with the passage 110. The removed materials may be carried to a collection area, such as a drainage bag 152, via the conduit 112. In some instances, the conduit 112 may be a length of flexible tubing.

The probe 102 is coupled to an actuator mechanism 107 disposed within the body 101. The actuator mechanism 107 is operable to ultrasonically vibrate the probe 102. In some instances, the actuator mechanism 107 may be a piezoelectric device. However, the actuator mechanism 107 may be any other mechanism or device operable to cause the probe 102 to vibrate ultrasonically. Vibration of the probe 102 may be altered by a user, such as a physician, before, during, or after a procedure. The hand piece 100 may be coupled to the surgical console 150, and vibration of the probe 102 may be adjusted, such as by interaction with the surgical console 150 or a peripheral thereof. In operation, the probe 102 may be brought into contact with the eye lens, and vibration of the probe 102 is utilized to break up and emulsify the lens for aspiration via the lumen 104.

The hand piece 100 may also include a sleeve 103. The sleeve 103 is coupled to a distal end of the body 101, and the probe 102 extends through a cavity 122 defined by the sleeve 103. The cavity 122 is coupled to a passage 115. Irrigation fluid is introduced into the passage 115, though an annular space 124 defined between an exterior of the probe 102 and an interior of the sleeve 103, and into the eye via one or more ports 126 formed in the sleeve 103 and/or a distal port 128 formed at a distal end of the sleeve 103. The irrigation fluid provided to the hand piece 100 may be supplied via a conduit 136, such as a length of flexible tubing, coupled to the hand piece 100. The conduit 136 may be coupled to a surgical console, such as surgical console 150, or some other irrigation fluid source. The irrigation fluid is used to irrigate the surgical site and suspend lens fragments for aspiration from the eye 121 via the passage 110.

The hand piece 100 may also include an integrated aspiration pump 106 disposed within the body 101. The pump 106 is operable to generate suction for drawing the aspiration flow into and through the probe 102 and along the aspiration passage 110 and towards the conduit 112. In some implementations, the pump 106 may include the length of flexible tubing 109, a shaft 118, and a motor 132 operable to rotate the shaft 118. The motor may be a DC motor or any other motor capable of rotating the shaft 118. The shaft may include a spiral protrusion 134 disposed on an outer surface of the shaft 118. The spiral protrusion 134 is adapted to squeeze the length of flexible tubing 109 so as to move material therein via a peristaltic action. However, the pump 106 may be any suitable pump operable to generate suction. As suction is applied to the eye 121 during operation of the pump 106, an aspiration flow is drawn into and through the probe 102 and along the passage 110 to the aspiration line 112. The aspiration flow may include the lens tissue fragments and irrigation fluid provided to the eye 121 during a surgical procedure.

The hand piece 100 may also include a check valve 120 in communication with the passage 110. The check valve 120 works in cooperation with a vacuum control system 154. The vacuum control system 154 and check valve 120 are operable to regulate vacuum pressure within the hand piece 100 at a desired pressure level. The vacuum control system 154 may include a filter 156, an accumulator 158, a pressure sensor 160, a vacuum pump 162, and a controller 163. In some instances, the filter 156 may be a porous hydrophobic filter. In other instances, though, the filter 156 may be any suitable filter.

Numerous types of valves may be utilized to form the check valve 120. For example, the check valve may be in the form of a diaphragm, disc, wafer, a ball-type valve, or other similar type of check valve that is adapted to open in response to a selected pressure within the passage 110. The check valve 120 is operable to open when the pressure within the passage 110 meets or falls below a selected pressure so as to substantially maintain the pressure within the passage 110 at or above a desired level. Although FIG. 1 illustrates the hand piece 100 as having a ball-type valve for the check valve 120, FIG. 1 merely illustrates an example implementation. As such, the disclosure is not so limited, and, as indicated above, the check valve 120 may be in the form of any of a number of different types of valves.

The check valve 120 may be a one-way check-valve that is configured to open when the pressure within the passage 110 reaches a selected level to provide fluid communication with the passage 110. The check valve 120 may open by dislodgement of a component of the check valve 120 (e.g., a diaphragm, ball, wafer, disc, or other closure/sealing mechanism). In the illustrated example, when the check valve 120 is opened, fluid communication between a vacuum line 164 and the passage 110 is created. That is, a ball 170 is dislodged opening the valve 120 when the pressure within the passage 110 drops below the selected pressure (as shown in FIG. 2). Such a configuration avoids the need to include a pressure sensor to detect the pressure within the passage 110, a controller to determine if the pressure is at or above the selected level, and an actuator to open a valve to relieve pressure.

Although the description of the operation of the check valve 120 is made with respect to a ball-type valve, as discussed above, the scope of the disclosure is not so limited. Referring to FIGS. 1 and 2, in operation, the pressure within the passage 110 during normal operation is above the pressure maintained within the vacuum line 164. Thus, under normal operation, the check valve 120 remains closed. However, fragments of the emulsified lens may clog or otherwise obstruct flow through the lumen 104, causing the pressure within passage 110 to rapidly decrease. This pressure may fall below the selected level. For example, pressure within the passage 110 may decrease in approximately 20 milliseconds due to an obstruction. In response to the pressure decrease within the passage 110 below the selected level, check valve 120 opens. In the particular example shown, the check valve 120 opens by dislocation of the ball 170. The ball 170 is shown in solid lines in its initial position. When dislocated, the ball 170 moves to its open position, depicted by the broken line 172. Once opened, the check valve 120 allows fluid to flow into the passage 110. The fluid introduced by a check valve may include a gas such as air or a liquid, such as a balanced salt solution.

In some instances, the fluid introduced into the passage 110 is provided via the vacuum line 164. The fluid within the vacuum line 164 passes through the filter 156 to remove impurities therefrom prior to entering the passage 110. Thus, the filter 156 may provide a sterile barrier that prevents or substantially reduces the risk of contamination from fluid entering the passage 110. As a result of the incoming fluid upon opening of the check valve 120, the pressure within the passage 110 is maintained approximately at the selected level. In other words, the check valve 120 opens to introduce a fluid into the aspiration passage 110 to substantially maintain the pressure within the hand piece at or above the selected level. Check valve 120 remains open until the pressure within the passage 110 increases above the selected pressure. For example, when the pressure within the passage 110 increases above the selected pressure, such as by dislodging of the material within the lumen 104, the ball 170 returns to its initial position, sealing the vacuum line 164.

Reaction of the check valve 120 to the changing pressure conditions within the passage 110 is almost immediate due the close proximity of the check valve 120 to the passage 110. Therefore, without the check valve 120, removal of the obstruction from the lumen 104 would result in a post occlusion surge in which a large quantity of aspirant is rapidly sucked through the passage 110 from the eye 121. Moreover, a post occlusion flow may result in damage to the eye, such as a rupture of the capsular bag or by contact of the eye with the probe 102 caused by a sudden movement of the eye associated with the post occlusion surge.

The selected pressure at which the check valve 120 is made to open may be established by vacuum control system 154. The vacuum pump 162 of the vacuum control system 154 may generate and maintain the selected pressure within the vacuum line 164 and the accumulator 158. The vacuum pressure generated by the vacuum pump 162 may be selected to be any desired pressure. The pressure sensor 160 senses a pressure within the accumulator 158. A signal that includes the sensed pressure is provided to the controller 163. The controller 163 compares the sensed pressure to the selected pressure. The selected pressure may be input by a user via an input device, such as a touch screen, knob, switch, keypad, or any other input device. If the controller 163 determines that the sensed pressure within the accumulator 158 is above the selected pressure, the controller 163 activates the vacuum pump 162 so as to reduce the pressure within the accumulator 158 and vacuum line 164 to the selected level.

The controller 163 may include a memory 165. The controller 163 may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions. The memory 165 may be a single memory device or a plurality of memory devices. Such a memory device may be a read-only memory, random access memory, volatile memory, non-volatile memory, static memory, dynamic memory, flash memory, cache memory, and/or any device that stores digital information. Note that when the controller 163 implements one or more of its functions via a state machine, analog circuitry, digital circuitry, and/or logic circuitry, the memory 165 storing the corresponding operational instructions may be embedded within, or external to, the circuitry comprising the state machine, analog circuitry, digital circuitry, and/or logic circuitry. The controller 163 is operable to received the sensed pressure signals, perform logic utilizing or associated with these signals, and generate control signals, such as vacuum pump control signals, to control operation of the vacuum pump 162.

The vacuum pressure within the vacuum line 164 holds the ball 170 against a sealing surface 174. For example, in some instances, the sealing surface 174 may be a rim of the vacuum line 164. The ball 170 contacts the sealing surface 174 to form a seal. When pressure within the passage 110 drops below the pressure within the vacuum line 164, the ball is separate from the sealing surface 174 permitting air to pass into the passage 110. Consequently, the pressure within the passage 110 is controlled to be the same or substantially the same as the pressure established within the vacuum line 164.

The accumulator 158 defines a volume that serves as a pressure storage reservoir. Consequently, the accumulator 158 enables to the vacuum control system 154 to react more quickly to a temporary demand and smoothes out pulsations, such as when the check valve 120 is opened and closed.

Placement of the check valve 120 substantially near the inlet of the aspirating pump 106 permits the fluid introduced via the check valve 120 upon opening to be drawn into the aspiration passage 110 upstream of the aspirating pump 106. This allows for the pressure level within the passage 110 to be increased and controlled. Consequently, the aspiration flow passing into and through the pump 106 is controlled such that, upon closure of the check valve 120, post occlusion flow is eliminated or substantially reduced, eliminating or dramatically reducing any effects of a post occlusion surge. Thus, the likelihood of injury to the eye is eliminated or substantially reduced.

Once the clog within the lumen 104 clears, such as when the fragments of lens tissue are reduced in size by ultrasonic vibrations provided by the actuator mechanism 107, the lower pressure within the vacuum line 164 draws the ball 170 back into contact with the sealing surface 174. As a result of the quick response of the check valve 120 to changing pressures within the passage 110 (e.g., on the order of 20 milliseconds), post occlusion surge is substantially reduced or eliminated. Further, the hand piece 100 is operable to quickly respond to changing pressure conditions within the passage 110 without the need of a pressure sensor in the hand piece 100 or any control regime to operate the check valve 120.

In some instances, the irrigation fluid introduced into the eye 121 via passage 115 can create a positive pressure at the surgical site within the eye 121. This positive pressure of the irrigation fluid can be adjusted by a user to a desired pressure. For example, this pressure may be set to approximately 0.5 to 1.0 psi. However, the pressure of the irrigation fluid may be set to any desired level. Generally, the irrigation fluid pressure is higher than the fluid pressure maintained in the vacuum line 164 and accumulator 158.

Figure 3:
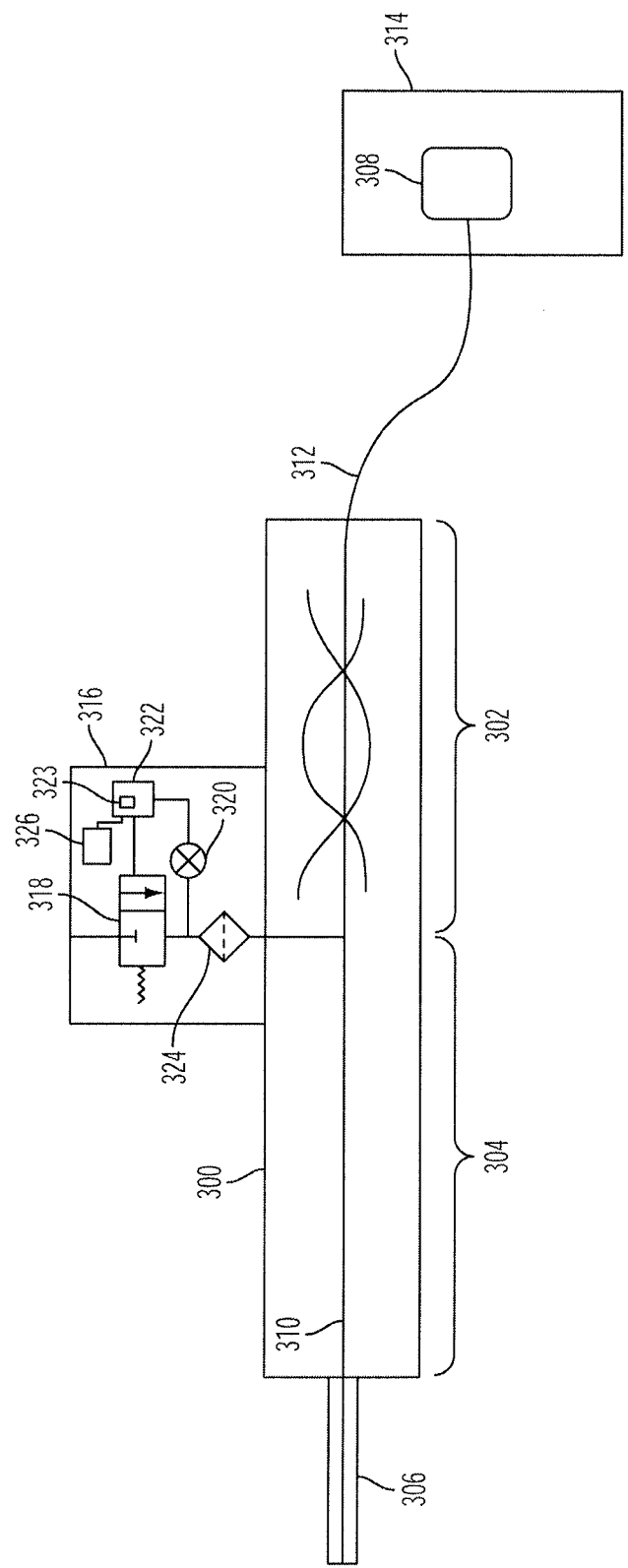
FIG. 3 shows another example hand piece operable to eliminate or substantially reduce post-occlusion flow.

FIG. 3 illustrates another example hand piece 300. Although shown in schematic form, the hand piece 300 may be similar to the hand piece 200. Hand piece 300 includes an integrated aspiration pump 302. The pump 302 may be similar to a type described herein as well as any other suitable pump. For example, the pump may include a length of flexible tubing that is squeezed by a spiral protrusion formed on an outer surface of a rotatable shaft. The pump 302 may also include a motor operable to rotate the shaft. Thus, the pump 302 may be a peristaltic pump.

The hand piece 300 also includes a phacoemulsification portion 304 and a tip 306. Similar to the hand piece 200, the phacoemulsification portion 304 may include an actuator mechanism operable to vibrate probe 306. For example, the phacoemulsification portion 304 may include an actuator mechanism operable to vibrate probe 306 ultrasonically. The actuator mechanism may be a piezoelectric device or any other mechanism or device operable to cause the probe 306 to vibrate and, particularly, vibrate ultrasonically. The hand piece 300 also includes a passage 310 extending from the probe 306 and through the phacoemulsification portion 304 and pump portion 302. The passage 310 is coupled to a conduit 312. The conduit 312 may be a length of flexible tubing or any other conduit. The conduit 312 is coupled to a collection area, such as drainage bag 308. The drainage bag 308 may be housed within a surgical console 314.

Similar to the hand piece 200, the hand piece 300 is operable to quickly to respond to a decrease in pressure caused by, for example, an obstruction formed in a lumen of the probe 306. To that end, the hand piece 300 also includes a pressure relief system 316. The pressure relief system 316 may include a valve 318, a pressure sensor 320, a controller 322, a filter 324, and a power source 326. The pressure sensor 320 senses a pressure within the passage 310. The sensed pressure information is provided to the controller 322. The controller 322 may be similar to controller 163 and may include a memory 323 similar to the memory 165. The controller 322 is operable to determine if the sensed pressure is at or below a selected pressure. The selected pressure may be set to be any desired pressure. If the pressure within passage 310 is at or below the selected pressure, the controller 322 is operable to open the valve 318. The pressure within the passage 310 may decrease below the selected pressure when an occlusion forms, for example, within a lumen of the probe 306. When opened, the valve 318 permits air to pass through the valve 318, the filter 324 and into the passage 310. The filter 324 may be similar to the filter 156. Consequently, the filter 324 is operable to remove impurities from the incoming air to prevent or substantially reduce the risk of contamination. The power source 326 is operable to provide power to all or any one of the controller 322 and valve 318. In some instances, the power source 326 may be a battery, capacitor, or any other device operable to store electrical power. In other instances, the power source 326 may be omitted, as power may be supplied from an external source. For example, in some instances, power may be provided from a surgical console to which the hand piece 300 is coupled.

The close proximity of the pressure relief system 316 to the passage 310 provides for a rapid response to changing pressure conditions therein. Consequently, when the occlusion clears, the pressure relief system 316 is operable to sense when the pressure rises above the selected pressure and close the valve 318 in response. The rapid response of the valve 318 to the rising pressure within the passage 310 upon clearance of the obstruction prevents or substantially reduces any post-occlusion surge through the hand piece 300. Thus, risk of injury to the eye is substantially reduced or eliminated.

The foregoing description generally illustrates and describes various implementations for the elimination or substantial reduction of post-occlusion surge within a hand piece. It will, however, be understood by those skilled in the art that various changes and modifications can be made to the above-discussed construction without departing from the spirit and scope of the disclosure, and that it is intended that all matter contained in the above description or shown in the accompanying drawings shall be interpreted as being illustrative, and not to be taken in a limiting sense. Furthermore the scope of the present disclosure shall be construed to cover various modifications, combinations, additions, alterations, etc., above and to the above-described examples, which shall be considered to be within the scope of the present disclosure. Accordingly, various features and characteristics as discussed herein may be selectively interchanged and applied to other illustrated and non-illustrated implementations, and numerous variations, modifications, and additions further can be made thereto without departing from the spirit and scope of the present disclosure.

What is claimed is:

1. A surgical hand piece comprising:
   a hand piece body;
   a probe operatively coupled to the hand piece body;
   an aspiration passage defined through the probe and hand piece body;
   an aspiration pump integrated within the hand piece body, the aspiration pump operable to generate an aspirated flow along the aspiration passage; and
   a check valve disposed within the hand piece body between the aspiration passage and a vacuum line that couples the check valve to a vacuum source, the check valve comprising:
      a moveable element; and
      a sealing surface formed by a rim of the vacuum line, the check valve in an open condition when the moveable element is separated from the sealing surface and in a closed condition when the moveable element contacts the sealing surface to form a seal,
   wherein the check valve is adapted to open when a pressure within the aspiration passage falls below a selected level of pressure, and
   wherein a gas introduced into the aspiration passage via the check valve is a filtered gas from the vacuum source.

2. The surgical hand piece of claim 1, wherein the check valve is operable to introduce the gas into the aspiration passage from the vacuum line coupled to the vacuum source, which is separate from the hand piece.

3. The surgical hand piece of claim 1, wherein the check valve is operable to permit fluid flow into the aspiration passage and to prevent fluid flow out from the aspiration passage.

4. The surgical hand piece of claim 1, wherein the aspiration pump further comprises a shaft and a motor operable to rotate the shaft.

5. The surgical hand piece of claim 1, wherein the check valve opens to introduce the gas into the aspiration passage to substantially maintain the pressure within the aspiration passage at approximately the selected level of pressure.

6. The surgical hand piece of claim 5, wherein the check valve is operable to close when the pressure within the aspiration passage increases above the selected level of pressure.

7. An aspirating hand piece comprising:
   a body comprising a phacoemulsification portion;
   an aspiration passage extending through the body;
   a partial vacuum line extending from and in fluid communication with the aspiration passage;
   an aspiration pump operable to generate an aspiration flow through the aspiration passage; and
   a check valve disposed between the aspiration passage and the partial vacuum line, the check valve in communication with the aspiration passage and adapted to open in response to a pressure condition within the aspiration passage, the check valve comprising:
      a moveable element; and a sealing surface formed by a rim of the partial vacuum line, the check valve in an open condition when the moveable element is separated from the sealing surface and in a closed condition when the moveable element contacts the sealing surface to form a seal, wherein the check valve is further in communication with a vacuum source, and wherein a gas introduced into the aspiration passage via the check valve is a filtered gas from the vacuum source.

8. The aspirating hand piece of claim 7, wherein, when open, the check valve is operable to permit the gas into the aspiration passage.

9. The aspirating hand piece of claim 7, wherein the check valve is operable to permit fluid flow into the aspiration passage and to prevent fluid flow out from the aspiration passage.

10. The aspirating hand piece of claim 7, further comprising a probe operatively connected to the phacoemulsification portion of the body and projecting therefrom, wherein the probe defines a lumen, and wherein the lumen is in communication with the aspirating passage.

11. The aspirating hand piece of claim 7, wherein the check valve is disposed within the body.

12. The aspirating hand piece of claim 7, wherein the check valve is operable to open when a pressure within the aspiration passage drops below a selected level so as to substantially maintain the pressure at or above the selected level.

13. The aspirating hand piece of claim 12, wherein the check valve is operable to permit the gas from the partial vacuum line coupled to the vacuum source, which is separate from the hand piece, into the aspiration passage.

14. The aspirating hand piece of claim 12, wherein the check valve is operable to remain open at least until the pressure within the hand piece approximates the selected level.

15. A surgical hand piece comprising:
a hand piece body;
a probe operatively coupled to the hand piece body;
an irrigation passage defined through the probe and hand piece body, the irrigation passage coupled to an irrigation conduit to receive irrigation fluid;
an aspiration passage defined through the probe and hand piece body;
an aspiration pump integrated within the hand piece body, the aspiration pump operable to generate an aspirated flow along the aspiration passage; and
a check valve disposed between the aspiration passage and a flexible vacuum conduit that couples the check valve to a vacuum source disposed outside the hand piece body, the check valve comprising:
a moveable element; and
a sealing surface, the check valve in an open condition when the moveable element is separated from the sealing surface and in a closed condition when the moveable element contacts the sealing surface to form a seal, and
wherein the check valve opens when a pressure within the aspiration passage falls below a selected pressure level, wherein a rim of the flexible vacuum conduit forms the sealing surface that cooperates with the moveable element to form a seal when the check valve is closed, and
wherein a gas introduced into the aspiration passage via the check valve passes through a filter before entering into the aspiration passage.

16. The surgical hand piece of claim 15, wherein the moveable element of the check valve comprises a ball that is freely moveable within a confined volume.

17. The surgical hand piece of claim 16, wherein the confined volume is defined between the sealing surface and the aspiration passage.

18. The surgical hand piece of claim 17, further comprising a drainage bag disposed within the console, the drainage bag being coupled to the aspiration passage by an aspiration conduit.

* * * * *